United States Patent [19]

Horrobin et al.

[11] Patent Number: 4,965,075
[45] Date of Patent: Oct. 23, 1990

[54] METHODS OF INCREASING 1-SERIES PGS IN THE BODY

[75] Inventors: David F. Horrobin, Surrey, England; Stephen C. Cunnane; Mehar S. Manku, both of Nova Scotia, Canada

[73] Assignee: Efamol Limited, Guildford, England

[21] Appl. No.: 273,680

[22] Filed: Nov. 21, 1988

Related U.S. Application Data

[63] Continuation of Ser. No. 783,601, Oct. 3, 1985, abandoned.

[30] Foreign Application Priority Data

Oct. 3, 1984 [GB] United Kingdom ................ 8425006

[51] Int. Cl.$^5$ ..................... A61K 33/34; A61K 31/20
[52] U.S. Cl. .................................. 424/638; 514/558; 514/866
[58] Field of Search ................ 424/141, 638; 514/558, 514/886, 887, 904, 905, 930, 866, 899

[56] References Cited

U.S. PATENT DOCUMENTS

| Re. 29,814 | 10/1978 | Snyder | 514/558 X |
| 4,216,236 | 8/1980 | Mueller et al. | 426/658 X |
| 4,237,118 | 12/1980 | Howard | 424/140 |
| 4,614,663 | 9/1986 | Rule | 426/607 X |
| 4,703,060 | 10/1987 | Traitler et al. | 514/866 X |

FOREIGN PATENT DOCUMENTS

| 0002341 | 6/1979 | European Pat. Off. | 514/887 |
| 1082624 | 9/1967 | United Kingdom . | |
| 1240513 | 7/1971 | United Kingdom . | |
| 1446431 | 8/1976 | United Kingdom . | |

*Primary Examiner*—John S. Maples
*Attorney, Agent, or Firm*—Nixon & Vanderhye

[57] ABSTRACT

Methods of influencing the 1-series/2-series PG balance in the body by administering a composition containing γ-linolenic acid and/or dihomo-γ-linolenic acid and assimilable copper compounds optionally with a diluent or carrier, the acids being as such or as derivatives convertible in the body thereto. The amounts of the acids or derivatives are 0.2 to 10 g (calculated as γ-linolenic acid) and of copper compounds are 0.1 to 100 mg (calculated as copper).

2 Claims, No Drawings

METHODS OF INCREASING 1-SERIES PGS IN THE BODY

This is a continuation of application Ser. No. 783,601, filed Oct. 3, 1985, now abandoned.

FIELD OF THE INVENTION

This invention relates to compositions of copper and fatty acids.

GENERAL

The administration of linoleic acid to animals or humans normally leads to the formation of γ-linolenic acid (GLA), dihomo-γ-linolenic acid (DGLA) and arachidonic acid (AA), and of the respective lipoxygenase and cyclo-oxygenase metabolites of these fatty acids including prostaglandins (PG's). The first step, the conversion of linoleic acid to GLA, is influenced by many factors. In order to raise the levels of metabolites along the essential fatty acid chain there are major advantages in the administration of GLA and/or DGLA in order to by-pass the inhibited linoleic/GLA step.

The lipoxygenase and cyclo-oxygenase products of GLA and DGLA metabolism have either desirable or neutral effects in a variety of situations. For example, PGE1 may desirably inhibit thrombosis, lower blood pressure, dilate blood vessels, prevent or attenuate inflammation in a variety of situations such as adjuvant arthritis in the rat, and inhibit the growth of animal and human cancer cells. Arachidonic acid in contrast produces a variety of both desirable and undesirable metabolites. Some like prostacyclin may have actions similar to those of PGE1 but others have highly undesirable effects such as promoting thrombosis and vasoconstriction, raising blood pressure, promoting inflammation and enhancing the growth of cancer cells. As discussed in the inventor Dr. Horrobin's previous patent applications including published European Specifications referred to later herein, to which reference may be made, there are therefore strong reasons for attempting to enhance the levels of DGLA and increasing the formation of its products while reducing or leaving unchanged the formation of AA and its products. In this way the balance between DGLA and AA metabolites may be moved in a favorably direction.

We have recently found that copper deficiency enhances while copper supplementation inhibits the formation of arachidonic acid in animals, possibly because copper inhibits the enzyme $\Delta^5$-desaturase which converts DGLA to AA. Rats were fed for 12 weeks on diets containing either adequate copper (6mg/kg food), deficient copper (1mg/kg food) or excess copper (250mg/kg food. At the end of this time the animals were killed and the fatty acid composition of plasma and liver phospholipids and liver triglycerides measured by gas chromatography. The results are shown in Table 1. As can be seen, copper deficiency consistently increases while copper supplementation reduces the ratio of AA to DGLA. Thus copper favorable influences the ratio between DGLA and AA.

TABLE 1.

The effects of copper deficiency, normal copper intake and copper excess on the DGLA and AA levels in plasma and liver total phospholipids and liver triglycerides in rats. Groups of 10 animals were fed the diets for 12 weeks. Results are expressed as mg/100mg total fat present and are the mean of 10 animals.

| Material | Plasma Phospholipids | | | Liver Phospholipids | | | Liver Triglycerides | | |
|---|---|---|---|---|---|---|---|---|---|
| Cu Status | D | N | E | D | N | E | D | N | E |
| DGLA Level | 0.1 | 0.9 | 0.8 | 0.3 | 1.3 | 1.6 | 0.5 | 0.4 | 0.4 |
| AA Level | 34.9 | 26.3 | 20.9 | 35.8 | 32.8 | 31.8 | 7.3 | 4.7 | 3.0 |
| AA/ DGLA Multiple | 349 | 29.2 | 26.1 | 119.3 | 25.2 | 19.9 | 14.6 | 11.8 | 7.5 |

D = Deficient
N = Normal
E = Excess

Thus, when administering linoleic acid, or especially GLA or DGLA, with a view to enhancing the DGLA-/AA ratio, a copper deficiency is harmful while an enhanced copper intake is helpful in increasing the ratio. Such a biochemical result will be particularly valuable in the treatment of inflammatory disorders, or cardiovascular and thrombotic disorders, of menstrual cycle disorders, of psychiatric disorders, breast and prostatic disorders, diabetes, endometriosis, nutritional deficiencies and of malignancy, and the invention lies both in compositions of assimilable copper compounds with the acids and in treatment of such conditions.

The outline of production of 1-series and 2-series PGs in the body is believed to be as shown in the following diagram;

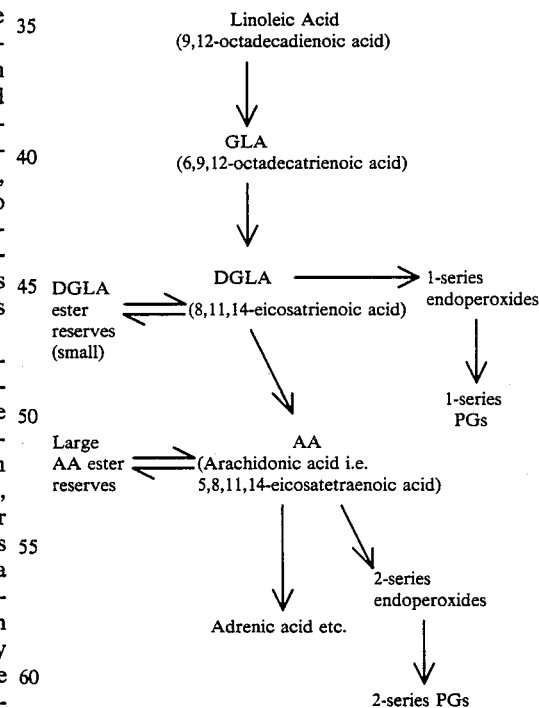

The broad outline of this pathway is well known, and it brings out clearly that a major function of essential fatty acids is to act as precursors for prostaglandins, 1-series PGs being formed from DGLA and 2-series PGs from arachidonic acid. Further, it has recently been found that the 22:4 n-6 acid produced from arachidonic acid gives rise to a series of homo-2-series PGs, though their importance is as yet unknown.

DGLA is the key substance. GLA is almost completely and very rapidly converted in the body to DGLA and so for practical purposes the oral administraiton of DGLA and GLA amounts to the same thing. DGLA can be converted to a storage form or to PGs of the 1-series or, through arachidonic acid, to PGs of the 2-series.

Considering dietary requirements, it is well known, for example, that linoleic acid cannot be made by the body and so must be taken in the diet. However, it has been generally thought that the body can metabolize linoleic acid to all the other n-6 acids and therefore that provided linoleic acid intake is adequate, no lack of the the other n-6 acids will be found.

In previous patent applications (for example Published European patent application No. A 0 003 407, U.S. Pat. No. 4 273 763; Published European patent application No. A 0 004 770, U.S. Pat. No. 4 309 415; Published European patent application No. 0 019 423, U.S. Pat. No. 4,388,324) it has, however, been pointed out that the first enzyme in the pathway, the $\Delta^6$-desaturase which, for example, converts linoleic acid to $\gamma$-linolenic acid, is not fully effective in a variety of conditions. The administration of $\gamma$-linolenic acid or dihomo-$\gamma$-linolenic acid or both has been suggested and has been successful in treating a variety of clinical conditions.

Particular reference should be made to the above specifications for the significance of a proper balance of 1-series and 2-series PGs in the body.

THE INVENTION

The invention provides pharmaceutically acceptable compositions of linoleic acid, $\gamma$-linolenic acid and/or dihomo-$\gamma$-linolenic acid and assimilable copper compounds optionally with a diluent or carrier, the said acids being as such or as derivatives convertible in the body thereto and the amounts of said acids or derivatives being 0.1 to 10g (calculated as $\gamma$-linolenic acid) and of said copper compounds 0.1 to 100mg (calculated as copper) or submultiple of said amounts convenient for daily administration thereof.

Preferably the amounts of said copper are 0.5 to 10mg or 100mg.

The invention further provides the use of acids and copper compounds as set out above for the preparation of medicaments for use in influencing the 1-series/2-series PG balance in the body in favor of 1-series PGs, in particular for the treatment of inflammatory disorders, cardiovascular disorders, menstrual cycle disorders and malignancy.

The invention still further provides a method of treatment for influencing said balance wherein a composition as set out above is administered to a person requiring such treatment.

Copper compounds to be used: any form of copper which can be assimilated into the body as shown by a rise in plasma and/or liver copper on feeding the compound to copper deficient animals, for example copper sulphate, copper acetate and copper gluconate.

DETAILS OF DERIVATIVES

The acids may be used as such or as pharmaceutically acceptable and physiologically equivalent derivatives as, for example, detailed later herein for GLA and DGLA, and reference to any of the acids is to be taken as including reference to the acids when in the form of such derivatives. Equivalence is demonstrated by entry into the pathways quoted herein, as evidenced by effects corresponding to those of the acids themselves or their natural glyceride esters. Thus, indirect identification of useful derivatives is by their having the valuable effect in the body of the acid itself, but conversion can be shown directly by gas chromatographic analysis of concentrations in blood, body fat, or other tissue by standard techniques, for example those of Pelick et al. p. 23, "Analysis of Lipids and Lipoproteins" Ed. Perkins, American Oil Chemists Society, Champaign, Ill., U.S.A.

In outline, the method includes extracting plasma samples (1 ml) with chloroform:methanol (2:1). The extract is filtered through sodium sulphate, evaporated to dryness, and taken up in 0.5 ml chloroform:methanol. The lipid fractions are separated by thin layer chromatography on silica gel plates. The phospholipid fraction, taken to reflect essential fatty acid contents most sensitively, is methylated using boron trifluoride-methanol. The resulting methyl esters of the fatty acids are separated and measured using a Hewlett-Packard 5880 gas chromatograph with a six foot column packed with 10% silar on chromosorb WAW 106/230. The carrier gas is helium (30ml/min). Oven temperature is programmed to rise from 165° C. to 190° C. at 2° C./min. Detector temperature is 220° C. and injector temperature 200° C. Retention times and peak areas are automatically computed by Hewlett-Packard Level 4 integrator. Peaks are identified by comparison with standard fatty acid methyl esters.

PACKS

If it is not desired to have compositions comprising different active materials together, packs may be prepared comprising the materials presented for separate, or part joint and part separate administration in the appropriate relative amounts, and use of such packs is within the purview of this invention.

DIETARY COMPOSITIONS

The invention is chiefly described n terms of methods of treatment and pharmaceutical compositions, but it will be understood that the $\gamma$-linolenic and other acids, and indeed the copper compounds, being in the nature of dietary supplements, could be incorporated in a dietary margarine or other foodstuff.

AMOUNTS OF $\gamma$- AND DIHOMO-$\gamma$-LINOLENIC ACIDS

A preferred daily dosage for an adult (weight ca 75kg) is from 0.1 up to 1, 2, 5 or even 10g as required $\gamma$-linolenic acid, or equivalent weight (calculated as $\gamma$-linolenic acid) of the acid such as dihomo-$\gamma$-linolenic acid or physiologically functional deriviative of either. Corresponding doses of Oenothera oil containing 8 to 10% of $\gamma$-linolenic acid, are easily calculated.

FORMS AND SOURCES OF $\gamma$-LINOLENIC AND OTHER ACIDS

Convenient, physiologically equivalent derivatives of $\gamma$-linolenic acid and dihomo-$\gamma$-linolenic acid for use according to the invention, as with the other acids, include salts, amides, esters including glyceride esters and alkyl (e.g. $C_1$ to $C_4$) esters, and phospholipids.

If desired, pharmaceutical compositions may be produced for use in the invention by associating the natural or synthetic acids, as such or as derivatives, with an acceptable pharmaceutical vehicle. It is, however, at present convenient to incorporate at least the γ-linolenic acid into compositions in the form of an available oil having a high γ-linolenic acid content, hence references to "oil" herein.

At the present time known natural sources of oils having a high γ-linolenic acid content are few (there are no known natural sources of significant amounts of dihomo-γ-linolenic acid). One source of oils currently available is the seed of Evening Primrose species such as *Oenothera biennis L.* and *Oenothera lamarckiana*, the oil extract therefrom containing γ-linolenic acid (about 8%) and linoleic acid (about 72%) in the form of their glycerides together with other glycerides (percentages based on total fatty acids). Other sources of γ-linolenic acid are Borage species such as *Borago officinalis* which, though current yield per acre is low, provide a richer source of γ-linolenic acid than Oenothera oil. Recent studies on fungi which can be cultivated by fermentation promise a fungal oil source.

The oil is extracted from the seed by one of the conventional methods of extraction such as cold pressure, screw pressure after partially cooking the seed, or solvent extraction.

Fractionation of a typical sample of this oil in the form of methyl esters shows the relative proportions:

| | |
|---|---|
| Palmitate | 6.15 |
| Stearate | 1.6 |
| Oleate | 10.15 |
| Linoleate | 72.6 |
| γ-Linolenate | 8.9 |

As a preservative, α-tocopherol is added to the oil in a concentration 0.1%.

The seed oil extracts referred to above can be used as such or can, for example, if desired, be fractionated to yield an oily composition containing the triglycerides of γ-linolenic acid and linoleic as the main fatty acid components, the γ-linolenic acid content being if desired a major proportion. Seed oil extracts appear to have a stabilising effect upon dihomo-γ-linolenic acid if present.

PHARMACEUTICAL PRESENTATION

The compositions according to the invention are conveniently in a form suitable for oral, rectal or parenteral administration in a suitable pharmaceutical vehicle, as discussed in detail for example in Williams British Patent Specification No. 1,082,624, to which reference may be made, and in any case very well known generally for any particular kind of preparation. Thus, for example, tablets, capsules, ingestible liquid or powder preparations, creams and lotions for topical application, or suppositories can be prepared as required. Injectable solutions of hydrolysed Oenothera oil may be prepared using albumin to solubilize the free acid.

Advantageously, a preservative is incorporated into the preparations. α-tocopherol in concentration of about 0.1% by weight has been found suitable for the purpose.

It will be understood that the absolute quantity of active materials present in any dosage unit should not exceed that appropriate to the rate and manner of administration to be employed but on the other hand should also desirably be adequate to allow the desired rate of administration to be achieved by a small number of doses. The rate of administration will moreover depend on the precise pharmacological action desired.

EXAMPLES

Soft gelatine capsules made by conventional methods are administered against conditions as set out herein wherein the 1-series/2-series PG balance in the body is disturbed as follows:

| Example 1 | | Example 2 | |
|---|---|---|---|
| GLA | 250 mg | DGLA | 100 mg |
| Copper | 2 mg | Copper | 0.5 mg |

| Example 3 | | Example 4 | |
|---|---|---|---|
| Evening Primrose Oil | 500 mg | Evening Primrose Oil | 750 mg |
| Copper | 1 mg | Copper | 0.5 mg |

The copper may be in the form of copper sulphate, copper acetate or copper gluconate or other assimilable copper compound.

A pack as referred to herein comprises 500 mg capsules of Evening Primrose Oil as above, to be taken 6/day, together with tablets of copper gluconate (0.5 mg copper) and inert carrier.

An alternative pack may comprise a topical ointment including Evening Primrose Oil, together with tablets of assimilable copper compound to be taken in the requisite amounts. Another pack may comprise a topical ointment including an assimilable copper compound, together with 500 mg capsules of Evening Primrose Oil to be taken in the requisite amounts.

Preparations of compositions as referred to herein is exemplified for example by the preparation of 500 mg capsules of Evening Primrose Oil as above with copper gluconate (0.5 mg copper).

We claim:

1. A method of influencing the 1-series/2-series PG balance in the body to increase the proportion of 1-series PGs, comprising administering to a person in need thereof a therapeutically effective quantity of a pharmaceutical composition comprising:
   (1) gamma-linolenic acid, dihomo-gamma-linolenic acid or a mixture of the two, present as such or as a derivative convertible in the body thereto, in an amount of from 0.2 to 10 grams, calculated as gamma-linolenic acid;
   (2) from 0.1 to 100 mg, calculated as copper, of at least one assimilable copper compound; and, optionally
   (3) a pharmaceutically acceptable carrier or diluent.

2. The method of claim 1, in which the amount of the copper compound is from 0.5 to 10 mg.

* * * * *